US012702571B2

(12) United States Patent
Friesen et al.

(10) Patent No.: US 12,702,571 B2
(45) **Date of Patent: *Aug. 11, 2026**

(54) PROSTHETIC FOOT

(71) Applicant: OTTOBOCK SE & CO. KGAA, Duderstadt (DE)

(72) Inventors: Jeff Friesen, Salt Lake City, UT (US); Nathan A. Williams, Salt Lake City, UT (US); Justin R. Smith, West Jordan, UT (US); Kelli D. Oborn, Erda, UT (US)

(73) Assignee: Ottobock SE & Co. KGaA, Duderstadt (DE)

( * ) Notice: Subject to any disclaimer, the term of this patent is extended or adjusted under 35 U.S.C. 154(b) by 1171 days.

This patent is subject to a terminal disclaimer.

(21) Appl. No.: 16/984,280

(22) Filed: Aug. 4, 2020

(65) Prior Publication Data

US 2020/0375765 A1 Dec. 3, 2020

Related U.S. Application Data

(63) Continuation of application No. 15/290,293, filed on Oct. 11, 2016, now Pat. No. 10,772,741, which is a continuation of application No. 13/511,763, filed as application No. PCT/US2010/057954 on Nov. 24, 2010, now Pat. No. 9,486,331.

(60) Provisional application No. 61/264,267, filed on Nov. 25, 2009, provisional application No. 61/264,274, filed on Nov. 25, 2009.

(51) Int. Cl.
*A61F 2/66* (2006.01)
*A61F 2/50* (2006.01)

(52) U.S. Cl.
CPC ........ *A61F 2/66* (2013.01); *A61F 2002/5003* (2013.01); *A61F 2002/5007* (2013.01); *A61F 2002/6614* (2013.01); *A61F 2002/6621* (2013.01); *A61F 2002/6642* (2013.01); *A61F 2002/665* (2013.01); *A61F 2002/6657* (2013.01); *A61F 2002/6678* (2013.01)

(58) Field of Classification Search
CPC ................ A61F 2/66; A61F 2002/5003; A61F 2002/5007; A61F 2002/6614; A61F 2002/6621; A61F 2002/6642; A61F 2002/665; A61F 2002/6657; A61F 2002/6678
See application file for complete search history.

(56) References Cited

U.S. PATENT DOCUMENTS 5,258,039 A * 11/1993 Goh .......................... A61F 2/66 623/55
5,376,141 A * 12/1994 Phillips ..................... A61F 2/66 623/38

(Continued)

*Primary Examiner* — Melanie R Tyson
*Assistant Examiner* — Melissa A Hoban
(74) *Attorney, Agent, or Firm* — WCF IP

(57) ABSTRACT

A prosthetic foot is provided with a forefoot spring, a heel spring and a base spring. The base spring is connected to the heel spring and to the forefoot spring. The base spring has receiving means for the forefoot spring and the heel spring, into which receiving means the heel spring and the forefoot spring can be inserted. The heel spring is connected to the forefoot spring via a coupling element, and the coupling element extends forwards along the forefoot spring at least via one portion thereof.

20 Claims, 12 Drawing Sheets

(56) References Cited

U.S. PATENT DOCUMENTS

| | | | | |
|---|---|---|---|---|
| 5,653,767 | A * | 8/1997 | Allen | A61F 2/68<br>623/55 |
| 5,944,760 | A * | 8/1999 | Christensen | A61F 2/66<br>623/55 |
| 6,929,665 | B2 * | 8/2005 | Christensen | A61F 2/66<br>623/55 |
| 2003/0120354 | A1 * | 6/2003 | Doddroe | A61F 2/66<br>623/38 |
| 2007/0100466 | A1 * | 5/2007 | Allert | A61F 2/66<br>623/55 |

* cited by examiner 9
9
8
5
51
22
7
34
32
43
3
44
11
4
52
10
521
31
6
1
21
2
24
42

42
44
4
43
431

43
44
42
4
421
46

1

5
3
4

6
2
24
26
521
31
11

9
9
5
71
6
2
73

PROSTHETIC FOOT

BACKGROUND OF THE INVENTION

Field of the Invention

The invention relates to a prosthetic foot with a forefoot spring, a heel spring and a base spring, the latter being connected to the heel spring and to the forefoot spring.

Background Description

U.S. Pat. No. 6,719,807 B2 describes a prosthetic foot with a two-dimensional resilient forefoot part, a two-dimensional resilient heel part, and a substantially rigid carrier part. One end of each of the forefoot part and heel part is connected to the carrier part, and the forefoot part and the heel part each work independently of the respective other part. The forefoot part extends forwards and substantially unidirectionally from its connection to the carrier part, while the heel part extends rearwards and substantially unidirectionally from its connection to the carrier part.

U.S. Pat. No. 5,181,933 describes a prosthetic foot with a securing means for facilitating the operation of engaging the foot with the stump of a prosthetic foot user. A large number of curved, energy-storing foot areas are secured on the securing means and extend downwards in order to rest on the ground. Each of the curved portions has an ankle area, the foot areas interact independently of each other with the ground, and the curved portions having a similar shape. A heel spring is secured in a releasable manner on a forefoot portion and extends rearwards. A similar construction is described in U.S. Pat. No. 5,514,185.

U.S. Pat. No. 5,776,025 describes a prosthetic foot with a securing area on which a downwardly extending, curved and partially slit spring is secured. A continuous spring with a heel area and a forefoot area is secured on the front lower end area of the spring. The continuous spring has a curved shape. A similar construction is described in U.S. Pat. No. 6,071,313.

US 2005/0203640 A1 describes a prosthetic foot with a resilient ankle area. Starting from an attachment adapter, an upper securing portion of the forefoot area extends obliquely rearwards and downwards and, after a curve, merges into a forwardly and downwardly extending arch portion, which ends in a toe portion. A heel spring extends in parallel as far as the ankle area, and, after the curve, a first portion assumes a greater inclination than the arch portion. The first portion is followed by another curve, such that a heel portion extends obliquely downwards and rearwards. The heel spring is therefore S-shaped. A lower base spring is connected to the rear end of the heel spring and to the toe area, and a cushion can be arranged between the toe portion and the front part of the base spring.

GB 306,313 describes a prosthetic foot with a U-shaped frame for attachment to a below-knee shaft, on which a heel part is arranged which is likewise U-shaped and is arranged at a right angle to the frame. A front part corresponding substantially to the contour of a natural foot is arranged on the heel part. The front part is mounted elastically via resilient rods.

U.S. Pat. No. 4,721,510 describes a prosthetic foot having a hollow elastomer cosmetic shell with a relatively large internal space. In the area of the insertion opening, the sole has a thickened area to which an anchor plate is secured. A reinforcement plate is arranged on the anchor plate, and a stiffening spring with a forefoot spring area and a heel spring area is secured on the reinforcement plate. Arranged above the spring is a wedge on which the springs bear in the event of overloading.

U.S. Pat. No. 4,822,363 describes a prosthetic foot with an elongate and curved spring which has a proximal securing branch and, adjoining the latter, a forwardly extending forefoot branch. Arranged on the securing branch, there is a heel spring, which is of a curved design, either approximately S-shaped or L-shaped. In an alternative embodiment, a heel spring is secured releasably in the forefoot area and extends rearwards with a slight curvature.

U.S. Pat. No. 2,475,372 describes a prosthetic foot with an upper area on which a below-knee shaft can be secured in an articulated manner. A metatarsal area is mounted in an articulated manner on a heel area. The metatarsal area is adjoined by a forefoot area that is articulated thereon. The forefoot area is mounted resiliently via a spring mechanism.

U.S. Pat. No. 5,258,039 describes a resilient prosthetic foot with a forefoot spring and a heel portion that are connected to each other by an elastomeric ankle element. The forefoot spring has a longitudinal slit. The heel spring has a C-shaped design. In an alternative embodiment, the prosthetic foot is designed in one piece.

U.S. Pat. No. 6,669,737 B2 describes a resilient foot insert for an artificial foot, comprising at least two springs which in a side view, in an unloaded state, enclose between them an approximately triangular space and form a roof area. A securing element is arranged in the roof area. Starting from the securing element, a heel portion extends rearwards and downwards in a concave curve, while a forefoot portion extends forwards and downwards in a similarly concave curve. A separate base spring is connected, in the heel area and in the toe area, to the heel portion and to the forefoot portion.

U.S. Pat. No. 6,099,572 describes a resiliently elastic foot insert with at least one leaf spring, which comprises at least two leaf spring elements which are coupled in parallel and are arranged next to each other. The leaf spring elements are connected to each other at both ends and, between the two end areas, have a clearance from each other. The connection is designed to be rigid in terms of torque in at least one of the two end areas.

SUMMARY OF THE INVENTION

The Otto Bock company has produced a resilient foot insert called the 1C30 Trias, in which a dual heel spring and a dual forefoot spring are secured on a proximal adapter. A base spring is secured on the rear end of the dual C-shaped heel spring. The base spring is likewise fixed to the front end of the forefoot spring.

It is an object of the present invention to make available a prosthetic foot that provides a comfortable rollover. Another object of the invention is to make available a prosthetic foot that can also be used on patients with a high activity level. Finally, a further object of the invention is to make available a prosthetic foot that is easy to produce and that can be easily adapted to different users.

According to the invention, these objects are achieved by a prosthetic foot having the features of the main claim. Advantageous embodiments and developments of the invention are set forth in the dependent claims.

In the prosthetic foot according to the invention, with a forefoot spring, a heel spring and a base spring, the latter being connected to the heel spring and to the forefoot spring, provision is made that the base spring has receiving means for the forefoot spring and the heel spring, into which receiving means the heel spring and the forefoot spring can be inserted. The receiving means permit a modular construction of the prosthetic foot and allow different base springs to be used that are adapted to the weight, the mobility grade and other aspects of the prosthesis user. They can be adapted very easily by inserting the forefoot spring and the heel spring into the respective receiving means. The receiving means can hold the forefoot spring and the heel spring with a form fit, such that there is no need for adhesive bonding or other forms of attachment in order to create a connection, and thus a force coupling, between the forefoot spring and the heel spring.

The receiving means can be designed as pockets into which the heel spring and the forefoot spring are inserted. In principle, no further locking is needed if the forefoot spring and the heel spring are tensioned in the assembled state and subject the receiving means to a force that forces the receiving means outwards, that is to say the rear receiving means rearwards and the front receiving means forwards.

The pockets can be of a closed design and have an insertion opening into which the forefoot spring and the heel spring are inserted. The closed design of the pockets provide protection for the sensitive end area of the springs, such that destruction, for example in the case of fibre-reinforced composite springs, is not to be expected. The insertion openings preferably lie opposite each other, such that the directions of insertion are counter to each other, which has the effect that the base spring is subjected to tension after insertion of the heel spring and the forefoot spring.

Pretensioning means optionally can be arranged in the receiving means that pretensions the heel spring and/or the forefoot spring against the base spring or the receiving means, in order to provide additional securing of the base spring on the forefoot spring and on the heel spring. The pretensioning means can be designed to include a spring or elastomer element and can provide pretensioning or an additional pretensioning of the forefoot spring and of the heel spring against the receiving means or the base spring. The pretensioning means can also form a clip connection to also permit a form-fit locking, such that the pretensioning elements can also serve as fixing means. Thus, locking means are also provided in the receiving means in order to lock the base spring to the forefoot spring and/or to the heel spring, in particular with a form-fit locking action. Corresponding locking means can be provided on the forefoot spring and the heel spring and engage with the locking means in or on the receiving means. Pretensioning elements can be cast into the receiving means, pushed in, bonded in or secured on the heel spring and/or the pretensioning means.

The base spring can be designed as a tension member, for example as a strap, which is flexible but not elastic against bending forces or moments and preferably not elastic in the longitudinal direction of the base spring.

The base spring can be designed as a spring, arching upwards in the unloaded state of the prosthetic foot, so as to permit inward deflection in the event of loading of the heel, loading of the forefoot or high axial loading, by means of the arch being reduced and the base spring lengthening. The stiffness of the base spring, and therefore the rollover of the prosthetic foot, can be influenced by the degree of arching.

The base spring can be pretensioned with a tensile stress in the unloaded state of the prosthetic foot, such that the ends of the base spring are forced in different directions. In the case of an arched base spring, an applied tensile stress also causes a bending moment within the spring.

The base spring can be designed as an injection-moulded part, especially when designed as a spring, in order to achieve rapid and inexpensive production. The base spring can also be designed in several parts and put together in a joining method, for example by several injection-moulded parts being connected to one another. It is also possible for the base spring to be made of different materials that are connected to one another by injection moulding. For example, spring elements or rigid components can be placed into the mould and encapsulated. It is also possible for individual components of the base spring to be placed into the injection-moulding tool and for other components to be injected thereon. The individual parts of the base spring can likewise be produced by multi-component injection moulding, for example by two-component injection moulding. The base spring can be produced from a composite material or can have parts that are made of a composite material. Examples of composite materials that can be used are fibre-reinforced plastics, for example plastics reinforced with carbon fibre or reinforced with glass fibre.

The base spring can have a curved middle portion, which is adjoined at both ends by the receiving means. The receiving means can be screwed on, clipped on or injected on. The receiving means can also be integrally formed on the middle portion. The middle portion can be designed, for example, as a beam spring made of a fibre-reinforced plastic, onto which receiving means are injected.

The heel spring can be connected to the forefoot spring via a coupling element, such that there is no direct join of the heel spring to the forefoot spring. The coupling element serves to make available a further adjustment element, since the design of the coupling element, both in terms of its elasticity and also its geometric nature, can be used to modify the resiliency characteristics of the prosthetic foot.

The forefoot spring and the coupling element can be arranged extending parallel to each other at least in part, such that they supplement each other in terms of their elasticity. The coupling element thus extends forwards along at least a part of the forefoot spring, and parallel to the forefoot spring, at least in the unloaded state. The coupling element can have an upwardly directed portion and a forwardly directed portion, such that a substantially L-shaped structural part is present which extends in a manner corresponding to the forefoot spring. The angle of opening of the L-shaped coupling element can be different than the angle of opening of the forefoot spring. The upwardly directed portion is likewise oriented substantially vertically, such that only a slight spring action is made available from the vertically oriented portion when a perpendicular downwardly acting load is placed on the prosthetic foot. The upwardly directed portion can have an S-shaped configuration, as a result of which its spring action can be strengthened.

The heel spring can be secured on a front area of the coupling element, so as to make available a sufficient length of the heel spring. The longer a spring is, the more sensitively it is able to react to loads occurring at its ends. Moreover, coupling the front area of the heel spring to the front area of the coupling element affords the possibility of also using the elasticity of the forwardly directed portion of the coupling element in order to obtain a comfortable heel strike.

The coupling element can extend forwards along at least part of the forefoot spring, and parallel to the forefoot spring, such that the coupling element provides an additional spring action via the forwardly directed portion. For this purpose, the coupling element is designed as a spring, for example made of a fibre-reinforced plastic.

The heel spring can be curved and, from its rear end, extends forwards and upwards and has a curvature such that the front end area is oriented substantially horizontally or at a slight downward incline. A precise setting of the spring characteristics can be achieved by means of the undulating design of the heel spring.

The forefoot spring can have a substantially straight forefoot portion which is oriented at a downward inclination towards the front and which, starting from the curve that follows the substantially vertically oriented portion, can extend forwards rectilinearly. In the toe area, it can have a flattening, which can also merge upwards into a slight curvature in order to facilitate rollover.

A connecting means can be provided for securing the prosthetic foot to a below-knee shaft and is arranged on the proximal end of the prosthetic foot. The connecting means can be secured, preferably by screwing, on the proximal end of the forefoot spring and, if appropriate, on the proximal end of the coupling element. The connecting means can be provided with a shock absorber which, in addition to axial forces, is also able to take up torques and absorb rotation movements.

The forefoot spring can be designed as a straight flat spring, with the connecting means arranged at a rear portion of the forefoot spring. The coupling element can be designed as a straight flat spring, too, arranged parallel to the forefoot spring. No vertical part of the coupling element or the forefoot spring is needed.

The forefoot spring and the base spring can have a slit that extends from the front end of the prosthetic foot, in order to permit a medial-lateral mobility of the forefoot spring and of the base spring. It is in this way possible, for example upon rollover on an inclined plane, that not just one edge establishes the contact with the ground or with the shoe.

The prosthetic foot can have a progressive ankle moment profile. A progressive ankle moment profile can be achieved through a combination of the heel spring with a resilience element. In particular, the shape of the resilience element can generate the progressiveness, by increasing the cross-sectional surface that is to be compressed. A progressive ankle moment profile can also be generated by placing the connecting area of the heel spring and of the coupling element on the base spring, but only with correspondingly high loading.

At heel strike, the force can be transferred at least partially to the forefoot spring via the base spring, this being achieved by the pretensioning and coupling of the forefoot spring to the heel spring via the base spring. The base spring thus serves as tension element, such that the force upon heel strike is transferred via the base spring to the forefoot spring. Energy is partially stored in the base spring especially in the embodiment as a base spring, particularly if the latter has an S-shaped curvature, and is then returned, since the connections and couplings of the springs to one another has the effect that none of them is able to act independently of the other springs.

The forefoot spring and the base spring, especially in the embodiment as a base spring, are designed, in terms of their shape and flexural elasticity, in such a way that during rollover, when the force is initially introduced into the ball region at the start of loading of the forefoot, the forefoot spring and the base spring come closer to each other by means of each of them bending under increasing loading. In this way, the springs can come to lie on each other, with the result that, starting from a defined loading level, the spring resistance can be increased by the springs lying on each other and by the friction of the springs on each other.

In the prosthetic foot according to the invention, with a forefoot spring, a heel spring and a base spring, the latter being connected to the heel spring and to the forefoot spring, provision is made that the heel spring is connected to the forefoot spring via a coupling element, such that there is no direct join of the heel spring to the forefoot spring. The coupling element serves to make available a further adjustment element, since the design of the coupling element, both in terms of its elasticity and also its geometric nature, can be used to modify the resiliency characteristics of the prosthetic foot. The coupling element extends forwards along the forefoot spring at least via one portion and makes available an optionally resilient portion on which the heel spring can be supported. The articulation of the heel spring on the coupling element decouples the heel spring from the forefoot spring, such that a more variable adjustment of the prosthetic foot can be carried out, since the points of articulation can be chosen more freely. The connection of heel spring and forefoot spring no longer has to be made at sites of high mechanical loading, and instead can be made at locations that can be chosen relatively freely.

The forefoot spring and the coupling element can be arranged extending parallel to each other at least in part, such that they supplement each other in terms of their elasticity. The coupling element thus extends forwards along at least a part of the forefoot spring, and parallel to the forefoot spring, at least in the unloaded state. The coupling element can have an upwardly directed portion and a forwardly directed portion, such that a substantially L-shaped structural part is present which extends in a manner corresponding to the forefoot spring. The angle of opening of the L-shaped coupling element can be different than the angle of opening of the forefoot spring. The upwardly directed portion is likewise oriented substantially vertically, such that only a slight spring action is made available from the vertically oriented portion when a perpendicular downwardly acting load is placed on the prosthetic foot. The upwardly directed portion can have an S-shaped configuration, as a result of which its spring action can be strengthened.

The heel spring can be secured on a front area of the coupling element, so as to make available a sufficient length of the heel spring. The longer a spring is, the more sensitively it is able to react to loads occurring at its ends. Moreover, coupling the front area of the heel spring to the front area of the coupling element affords the possibility of also using the elasticity of the forwardly directed portion of the coupling element in order to obtain a comfortable heel strike.

The coupling element can extend forwards along at least part of the forefoot spring, and parallel to the forefoot spring, such that the coupling element provides an additional spring action via the forwardly directed portion. For this purpose, the coupling element is designed as a spring, for example made of a fibre-reinforced plastic.

The heel spring can be curved and, from its rear end, extends forwards and upwards and has a curvature such that the front end area is oriented substantially horizontally or at a slight downward incline. A precise setting of the spring characteristics can be achieved by means of the undulating design of the heel spring.

The forefoot spring can have a substantially straight forefoot portion which is oriented at a downward inclination towards the front and which, starting from the curve that follows the substantially vertically oriented portion, can extend forwards rectilinearly. In the toe area, it can have a flattening, which can also merge upwards into a slight curvature in order to facilitate rollover.

The base spring can have receiving means for the forefoot spring and the heel spring, into which receiving means the heel spring and the forefoot spring can be inserted such that, in the assembled state, the forefoot spring and the heel spring are inserted and held in the receiving means. The receiving means permit a modular construction of the prosthetic foot and allow different base springs to be used that are adapted to the weight, the mobility grade and other aspects of the prosthesis user. They can be adapted very easily by inserting the forefoot spring and the heel spring into the respective receiving means. The receiving means can hold the forefoot spring and the heel spring with a form fit, such that there is no need for complicated adhesive bonding or other forms of attachment in order to create a connection, and thus a force coupling, between the forefoot spring and the heel spring.

The receiving means can be designed as pockets into which the heel spring and the forefoot spring are inserted. In principle, no further locking is needed if the forefoot spring and the heel spring are tensioned in the assembled state and subject the receiving means to a force that forces the receiving means outwards, that is to say the rear receiving means rearwards and the front receiving means forwards.

The pockets can be of a closed design and have an insertion opening into which the forefoot spring and the heel spring are inserted. The closed design of the pockets provides protection for the in some cases sensitive end area of the springs, such that destruction, for example of the fibre structure in the case of fibre-reinforced composite springs, is not to be expected. The insertion openings preferably lie opposite each other, such that the directions of insertion are counter to each other, which has the effect that the base spring is subjected to tension after insertion of the heel spring and of the forefoot spring.

BRIEF DESCRIPTION OF THE DRAWINGS

Illustrative embodiments of the invention are explained in more detail below with reference to the attached figures.

DETAILED DESCRIPTION OF A PREFERRED EMBODIMENT OF THE INVENTION

Figure 1:
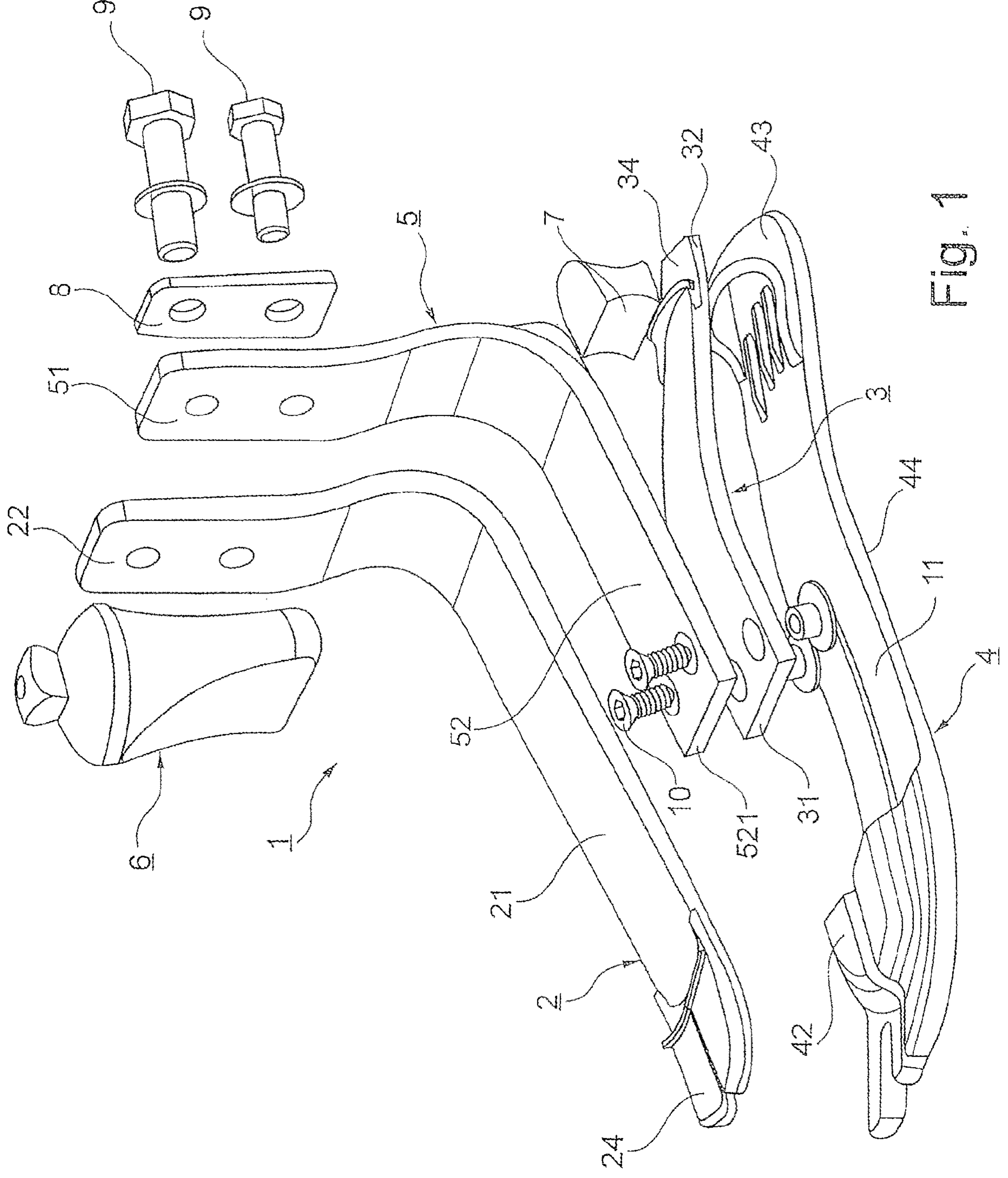
FIG. 1 shows a prosthetic foot in an exploded and perspective view.

In FIG. 1, a prosthetic foot 1 comprising a forefoot spring 2, a heel spring 3 and a base spring 4 in form of a base spring is shown in an exploded and perspective view. The forefoot spring 2 has a substantially straight vertical portion 22 which, after a curvature, merges into a substantially straight forefoot portion 21. The forefoot portion 21 extends forwards at a downward incline and can have a further bend in the toe area, such that the toe area is oriented substantially horizontally or is curved slightly upwards. In the front end area of the forefoot portion 21, sleeves or caps 24 can be arranged which at least partially enclose the forefoot spring 2. The forefoot spring 2 can be made of a plastic or of a composite material, in particular a fibre-reinforced plastic. A connecting means 6 in the form of a conventional adapter is positioned on the vertical portion 22. It is secured by bolts 9, which are guided through a securing plate or reinforcement plate 8. The bolts 9 pass through the reinforcement plate 8, a coupling element 5 and the vertical portion 22 of the forefoot spring 2 and are screwed into the adapter 6.

By means of the bolts 9, the forefoot spring 2 is coupled mechanically to the coupling element 5 in the proximal area of the vertical portion 22. The coupling element 5 likewise has a vertical portion 51, which is adjoined by a forwardly directed portion 52. The transition between the vertical portion 51 and the front portion 52 is likewise effected via a bend, which is arranged in the area of the natural ankle. The coupling element is likewise designed as a spring and extends with the front portion 52 substantially parallel to the forefoot portion 21 of the forefoot spring 2.

A front area 521 of the coupling element 5 is provided with bores through which screws 10 are guided. In the front area 521 of the coupling element 5, the screws 10 provide a mechanical connection to the front end area 31 of the heel spring. The front end area 31 of the heel spring 3 is likewise provided with bores or recesses through which the screws 10 extend, and the screws 10 are fixed in sleeves 11.

The heel spring 3 is designed with a slight curve and slopes gently downwards in the front end area, whereas the curvature extends in the opposite direction at the rear end 32 of the heel spring, such that there is a substantially horizontal orientation in the rear end 32. A spring element 7 in the form of an elastomer component is arranged between the heel spring 3 and the ankle area of the coupling element 5.

The rear end 32 of the heel spring 3 can likewise be lined with a sleeve or cap 34, which can be inserted into a rear receiving means 43 of the base spring 4.

The receiving means 43 of the one-piece base spring 4 is designed as a pocket, which forms a closed cap. The base spring 4 is arched slightly upwards and also has, at the front end, receiving means 42 for receiving the forefoot spring 2. The design of the forefoot spring 2 and also of the base spring 4 is explained in more detail below.

Figure 2B:
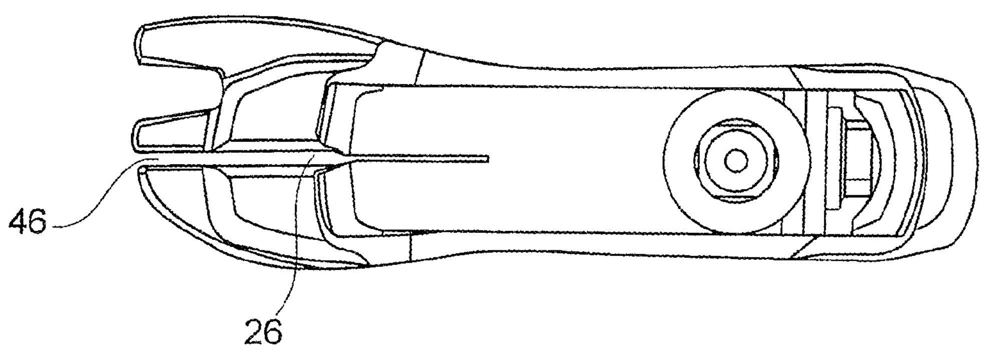
FIG. 2*b* shows a plan view of the prosthetic foot according to FIG. 1.
Figure 2A:
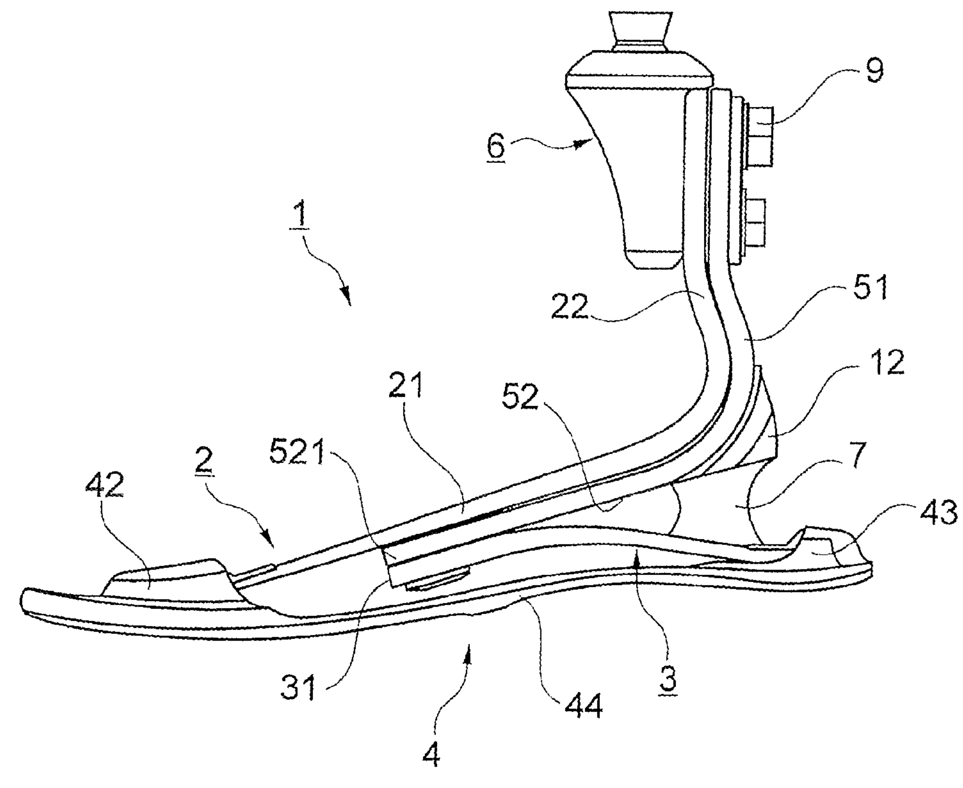
FIG. 2*a* shows a side view of a prosthetic foot according to FIG. 1.

FIG. 2*a* shows the prosthetic foot 1 in the assembled state. It will be noted that the bolts 9 extend through both the coupling element 5 and also the forefoot spring 2 and engage in threads in the adapter element 6. The vertical portions 22, 51 of the forefoot spring 2 and of the coupling element 5 extend parallel to each other and substantially vertically, both vertical portions 22, 51 being adjoined by a bent ankle area that has a curvature, for example a smooth curvature in the shape of a sector of a circle. The forwardly directed portion 52 of the coupling element 5 extends along part of the length of the forefoot portion 21, parallel to the forefoot portion 21, and can either bear on the underside of the forefoot portion 21 or have a small gap between itself and the forefoot portion 21. A wedge 12 in the ankle area of the coupling element 5 has a straight underside, such that, after the start of the curvature in the ankle area, there is a rectilinear continuation for supporting the spring element 7.

It will also be seen from FIG. 2*a* that the screws 10 end flush on the upper face of the front area 521 of the coupling element 5 and extend through both the coupling element 5 and also the heel spring 3. The heel spring 3 has an upwardly curved profile and extends rearward beyond the vertical portion 22, 51 of the forefoot spring 2 and of the coupling element 5. The rear end 32 is received in the receiving means 43 of the base spring 4. The base spring 4 has a slight upward curvature so as to be able to lengthen at heel strike, in order to provide an additional spring action. The front end of the base spring 4 is likewise provided with a receiving means 42, into which the front end of the forefoot area 21 of the forefoot spring 2 engages with a form fit.

In the assembled state shown, the front end of the forefoot spring 2 and the rear end 32 of the heel spring 3 press in different directions against the receiving means 42, 43 designed as pockets, such that the forefoot spring 2 and the heel spring 3 are tensioned against each other. This has the effect that the base spring 4 is under tensile stress, such that the upwardly directed arch tends to be pressed down. The tension between the heel spring 3 and the forefoot spring 2 is applied and maintained via the resilient coupling element 5. It will be seen from the plan view in FIG. 2*b* that both the base spring 4 and also the forefoot spring 2 have a slit 46, 26 that extends along approximately the first third of the forefoot spring 2. By means of the slits 26, 46, it is possible to permit and to compensate for different loading in the medial-lateral direction in the forefoot area.

Figure 3:
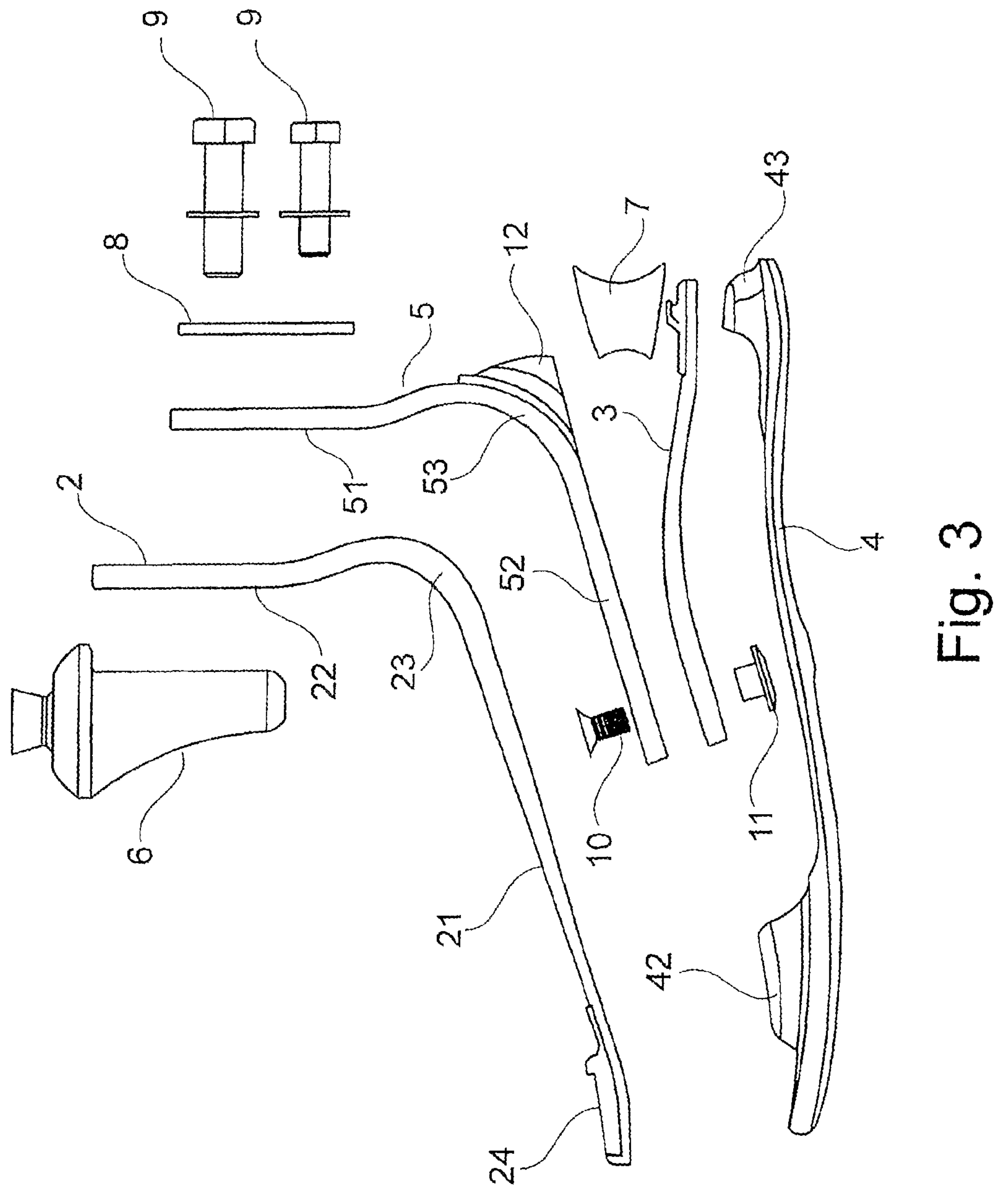
FIG. 3 shows an exploded side view of the prosthetic foot according to FIG. 2*a;*

FIG. 3 shows an exploded and perspective side view of the prosthetic foot 1. The figure clearly shows the forefoot spring 2 with the vertical portion 22, the curved ankle portion 23 in the shape of a sector of a circle, the forefoot area 21 and the sleeves 24 for insertion into the front receiving means of the base spring 4. The adapter 6 with the pyramid connector for connection to the other components of a prosthesis is mechanically secured, together with the coupling element 5, on the vertical portion 22 of the forefoot spring 2 by means of the bolts 9 and the reinforcement plate 8. The coupling element 5, which can also be designated as a securing spring, also has a vertical portion 51, a forwardly inclined front portion 52 and an ankle portion 53, which is designed corresponding to the ankle portion 23 of the forefoot spring 2. Arranged on the outer side of the curve is the wedge 12, which is provided as a continuation and bearing for an additional spring element 7. Instead of a spring element 7, it is also possible to provide a wedge-shaped spring element 7', as shown in FIGS. 3*a* and 3*b*, that prevents or restricts relative movement between the ankle area 53 and the wedge 12 to the rear end of the heel spring 3.

Figures 3A, 3B:
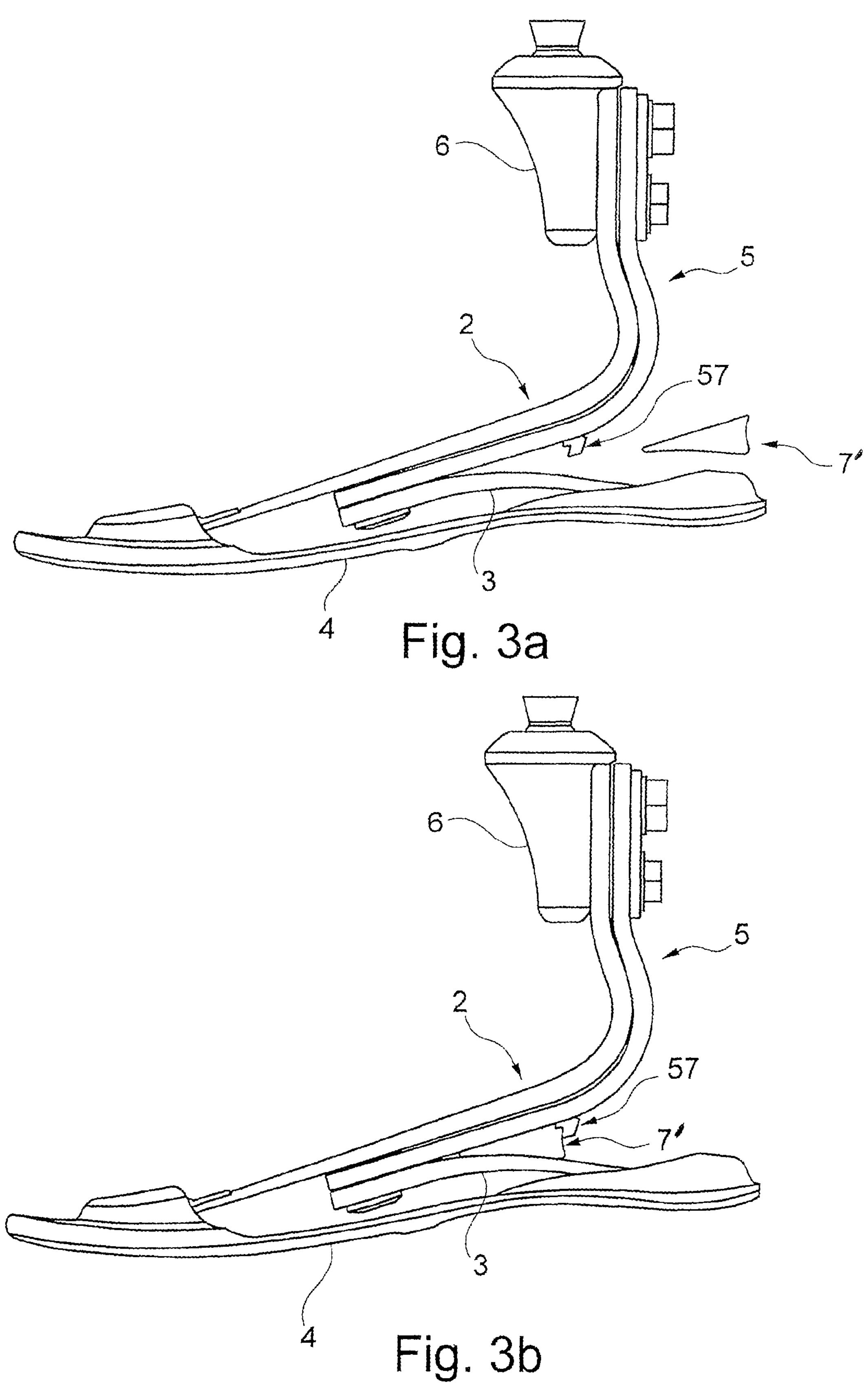
FIGS. 3*a*, 3*b* show variants of the FIG. 3 embodiment.

FIGS. 3*a* and 3*b* show a variant of the embodiment according to FIG. 3 in an assembled state. In FIGS. 3*a* and 3*b*, the spring element 7 has been replaced with a wedge-shaped spring element 7'. In FIG. 3*a* the spring element 7' is not inserted. The prosthetic foot can be used without the spring element 7', if the patient prefers a "soft" heel. For fixing the spring element 7' a retainer element 57 in form of a protrusion is provided at the coupling element 5. The wedge-shaped spring element 7' is inserted or slid in the tapered gap between the coupling element 5 and the heel spring 3 and is held there form-fittingly by the retainer element 57. The assembled state is shown in the FIG. 3*b*. With such an installed spring element 7 it is possible to vary the stiffness of the heel. With an installed spring element 7' a stiffer heel is provided than without the spring element 7'. Various different stiffnesses of the spring element 7' can be provided to adopt the stiffness of the prosthetic foot to the preferences of the patient during the tread.

Figures 4A, 4B:
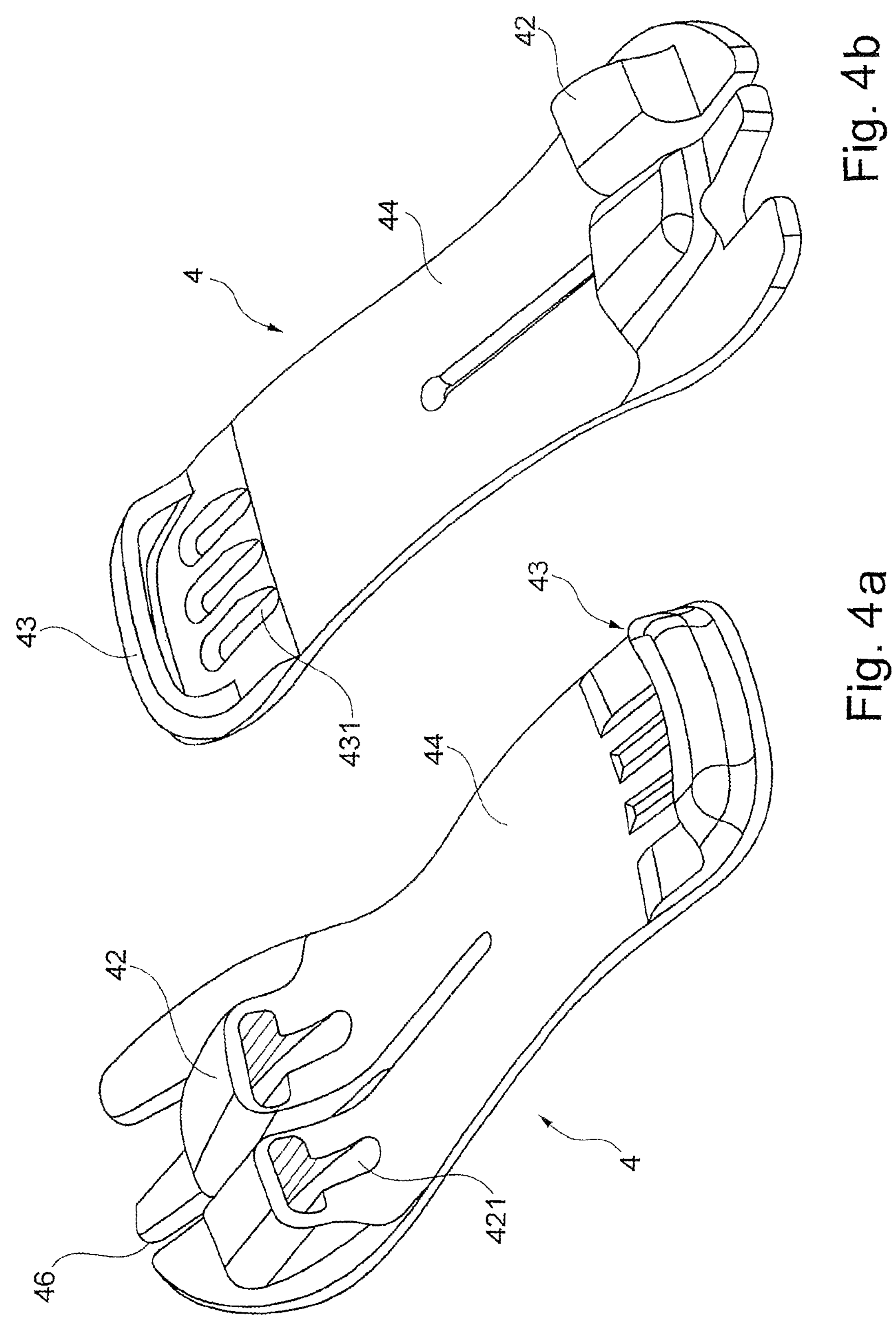
FIGS. 4*a*, 4*b* show a base spring in two perspective views.

FIGS. 4*a* and 4*b* show different views of a base spring 4. The base spring 4 has front and rear receiving means 42, 43 with insertion openings 421, 431, such that the respective portions 24, 34 of the forefoot spring 2 and of the heel spring 3 can be inserted and held with a form fit in the receiving means 42, 43. The slit 46, which is formed almost to the halfway point of the base spring 4, permits a medially/laterally directed compensating movement. In the middle portion 44 of the base spring, an arch is provided which is directed upwards in order to make available an additional spring action. Locking elements, tensioning elements or form-fit elements can be arranged in the receiving means 42, 43 so as to be able to hold the springs 2, 3 securely in the receiving means 42, 43. These locking elements can be designed as projections, for example, and the pretensioning means can likewise be designed as springs or elastomer elements that are arranged in and/or on the receiving means 42, 43. Because of the arrangement of the slit 46 in the base spring 4, two receiving means 42 are provided in the forefoot area of the base spring 4. In a design of the forefoot spring without a slit, only one receiving means 42 is provided and needed. The base spring 4 can be made from an injection moulded part and be designed in one piece. It is also possible for a reinforcing element, for example a curved and fibre-reinforced plastic spring, to be placed in an injection mould and then encapsulated with a plastic, such that the receiving means 42, 43 are formed integrally on the base spring. It is also possible in principle for the base spring 4 to be designed in several pieces, such that the receiving means 42, 43 are secured on the middle portion 44, for example by screwing, adhesive bonding, welding or some other way.

Figures 5A, 5B:
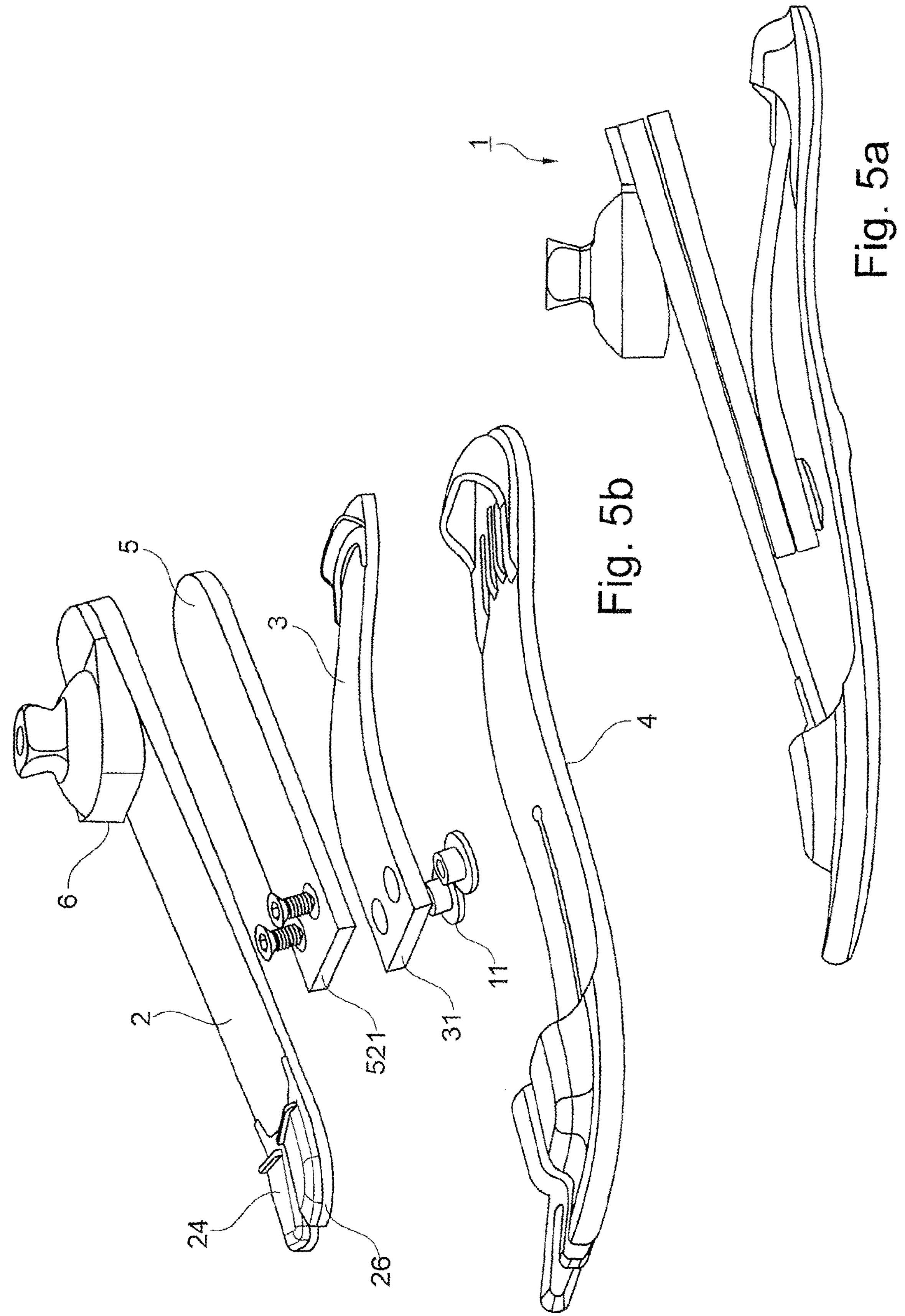
FIG. 5*a* shows a side view of an alternative embodiment of the prosthetic foot.
FIG. 5*b* shows an exploded and perspective view of the prosthetic foot according to FIG. 5*a;*

FIGS. 5*a* and 5*b* show an alternative embodiment of the invention. The basic structure of the prosthetic foot 1 corresponds to that shown in FIGS. 1 to 4. Identical reference signs designate identical structural parts. In contrast to the design according to FIGS. 1 to 4, the prosthetic foot 1 according to FIGS. 5*a* and 5*b* does not have a vertical portion 22, 51 on the forefoot spring 2 and the coupling element 5. The forefoot spring 2 and the coupling element 5 are thus designed as substantially straight springs, and the adapter 6 is once again secured by screws that pass through the coupling element 5 and the forefoot spring 2. Such a prosthetic foot is of advantage when there is a considerable below-knee length and when, as a result, the upper attachment point of the prosthetic foot 1 cannot be moved upwards to the desired extent. In addition, the adapter 6, at the surface facing the forefoot spring 2, is rounded or has a haunch so that there is no edge or rim facing to the upper surface of the forefoot spring. If a rim or edge is acting on the upper surface of the forefoot spring 2 and the adapter 6 is moved relatively to the forefoot spring, very high stress is applied to the forefoot spring, which is usually made of fiber composite material. By pressing a rim or edge onto the surface of the spring, a very small indentation is made, which may lead to a weakening of the material and to wear of the forefoot spring. With a rounded and smooth surface of the adapter 6, a kind of wedge is created in which an elastomer can be integrated.

Figures 6A, 6B:
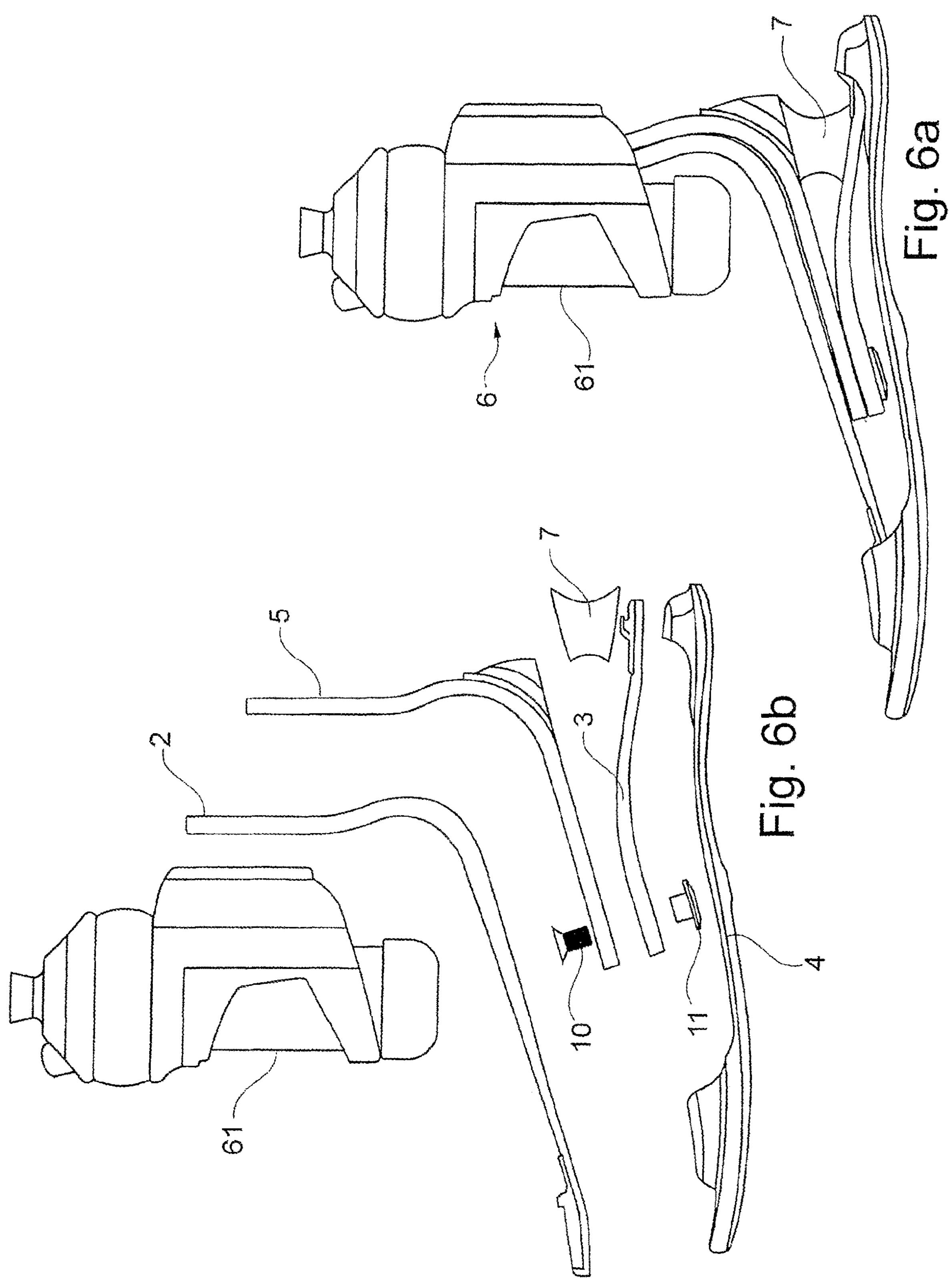
FIG. 6*a* shows a side view of a further alternative embodiment of the prosthetic foot with a shock absorber.
FIG. 6*b* shows an exploded view of the foot according to FIG. 6*a;*

FIGS. 6*a* and 6*b* show an alternative embodiment of the invention. The basic structure of the prosthetic foot 1 corresponds to that in FIGS. 1 to 4. In addition to the customary adapter 6, a shock absorber 61 is also provided that is able to take up axial loads and torques about the vertical axis. The shock absorber 61 serves to further increase the comfort level and affords further possibilities of adjustment, to ensure that the rollover can be adapted to the wishes of the prosthetic foot user. The stiffness can be adjusted by exchanging the absorption element for one with greater stiffness or by increasing the pretensioning in the absorption element of the shock absorber 61. The shock absorber 61 can also comprise a vacuum pump.

The base spring 4 is easy to produce and can be easily exchanged. It is thus possible to adapt the prosthetic foot 1 to the requirements of the particular user. It is set up in a simple way, by inserting the front ends of the forefoot spring 2 with the caps 24 into the front receiving means 42 and by inserting the rear end of the heel spring 3, if appropriate with a cap, into the rear receiving means 43, such that the base spring 4 is held securely on the prosthetic foot 1 as a result of the tension between the front and rear ends of the forefoot spring 2 and heel spring 3. At heel strike, the force is transferred at least partially to the forefoot spring 2, by means of the arch, in the middle area 44, stretching until the base spring 4 transfers tensile forces without deformation directly to the receiving means 42, which then in turn transfers forces to the forefoot spring 2. It is thus possible for all of the spring elements, namely the forefoot spring 2, the coupling element 5, the heel spring 3 and the base spring 4, to be utilized at heel strike in order to store and then deliver kinetic energy. This has the effect that all of the individual spring elements 2, 3, 4, 5 are coupled to one another and contributes to storing energy, such that each individual spring element 2, 3, 4, 5 can be made smaller than would be the case if it had to perform only partial functions in isolation.

The prosthetic foot 1 according to the invention has five main components, namely the forefoot spring 2, the coupling element 5, which is secured on the forefoot spring 2, the heel spring 3, which is secured on the coupling element 5, the base spring 4, which connects the front end 21 of the forefoot spring 2 to the rear end 32 of the heel spring 3, and the fifth component, the adapter element 6, which is designed as a conventional pyramid adapter with elements for securing to other components of a prosthetic leg. The springs 2, 3, 4, 5 are preferably made from fibre-reinforced plastic materials, in particular carbon-fibre-reinforced plastics, which are configured as so-called composite materials. The cross section of the springs 2, 3, 4, 5 is preferably rectangular or almost rectangular, a bend or deformation being effected preferably only in one plane. At the end areas, caps 24, 34 or protective elements can be provided for the springs. The base spring 4 can contain a core made of composite material. The base spring 4 with an upwardly directed arch, i.e. oriented towards the adapter 6, is moved or forced into a straight shape by application of a tensile force or of a bending moment. A spring action is achieved in this way. Such a base spring 4 provides a smooth rollover movement during mid-stance, on account of a plantar flexion of the toe area during loading of the heel, since the front end 21 of the forefoot spring 2 is drawn down when the heel strike occurs. The base spring 4 increases the energy return, both of the forefoot spring 2 and also of the heel spring 3, and thus provides a satisfying sensation when walking, because of the additional spring resistance. This is achieved by the excursion of the springs on account of the uniform load distribution resulting from the connection of the base spring 4 both to the forefoot spring 2 and also to the heel spring 3. As has already been discussed, the base spring 4 also increases the stability of the prosthetic foot 1, because the applied loads are divided up between the four spring components 2, 3, 4, 5. Overall, this has the effect that the prosthetic foot 1 has the features of an ankle joint, without having to accept any of the disadvantages of a traditional ankle joint, such as wear, complex construction, costs and maintenance.

The coupling element 5 has a number of advantages, for example the fact that the length of the heel support is extended, which leads overall to increased flexibility. The coupling element 5 reduces the load in the area of the attachment to the heel spring 3, which again leads to increased stability. The coupling element 5 further serves as an overload spring if unusually high loads occur. In the event of unusually high loads, the coupling element 5 can come into contact with the forefoot spring 2 in the front area or with the base spring 4, depending on the nature of the load that is applied. In this way, the direction in which the load is introduced is changed, which leads to an increased load-bearing capacity of the entire prosthetic foot 1.

The slit base spring 4 and the slit forefoot spring 2, with the orientation of the slit 26, 46 in the anterior-posterior direction, permit increased medial-lateral mobility of the prosthetic foot 1, which in turn leads to improved adaptability of the tread surface on the ground. The improved adaptability to the ground surface increases the comfort and stability experienced by the person using the prosthetic foot 1.

With the prosthetic foot 1, various configurations of the springs with different degrees of stiffness can be used, so as to be able to adapt to different weight categories for a defined size of the prosthetic foot 1. The modular, reversible mode of construction allows the prosthetic foot 1 to be dismantled for maintenance purposes, such that defective individual parts can be replaced and such that the prosthetic foot 1 can be adapted to a change of weight, to a change of loads, to a change in the degree of mobility or to the individual requirements of the users. It can be adapted easily by using a spring with a different degree of stiffness. The modular, reversible design permits a simplified assembly procedure, since the individual components are screwed together or fitted into one another. Adhesive bonding of the individual components of the prosthetic foot is no longer necessary, although this can be carried out in the area of the receiving means 42, 43 in order to reduce wear.

Adapting the degree of stiffness of the prosthetic foot 1 is mainly achieved by changing the thickness of the individual springs 2, 3, 4. The thicker a spring is, the stiffer it is, unless changes are made. It has therefore proven advantageous that the receiving means 42, 43 in the base spring 4 have identical dimensions, which are preferably adapted to the maximum stiffness, and that adaptation to the respective spring dimension is effected using compensating elements that are fitted onto the springs, cast onto the springs or fitted into the receiving means or injected in before assembly.

Figure 7:
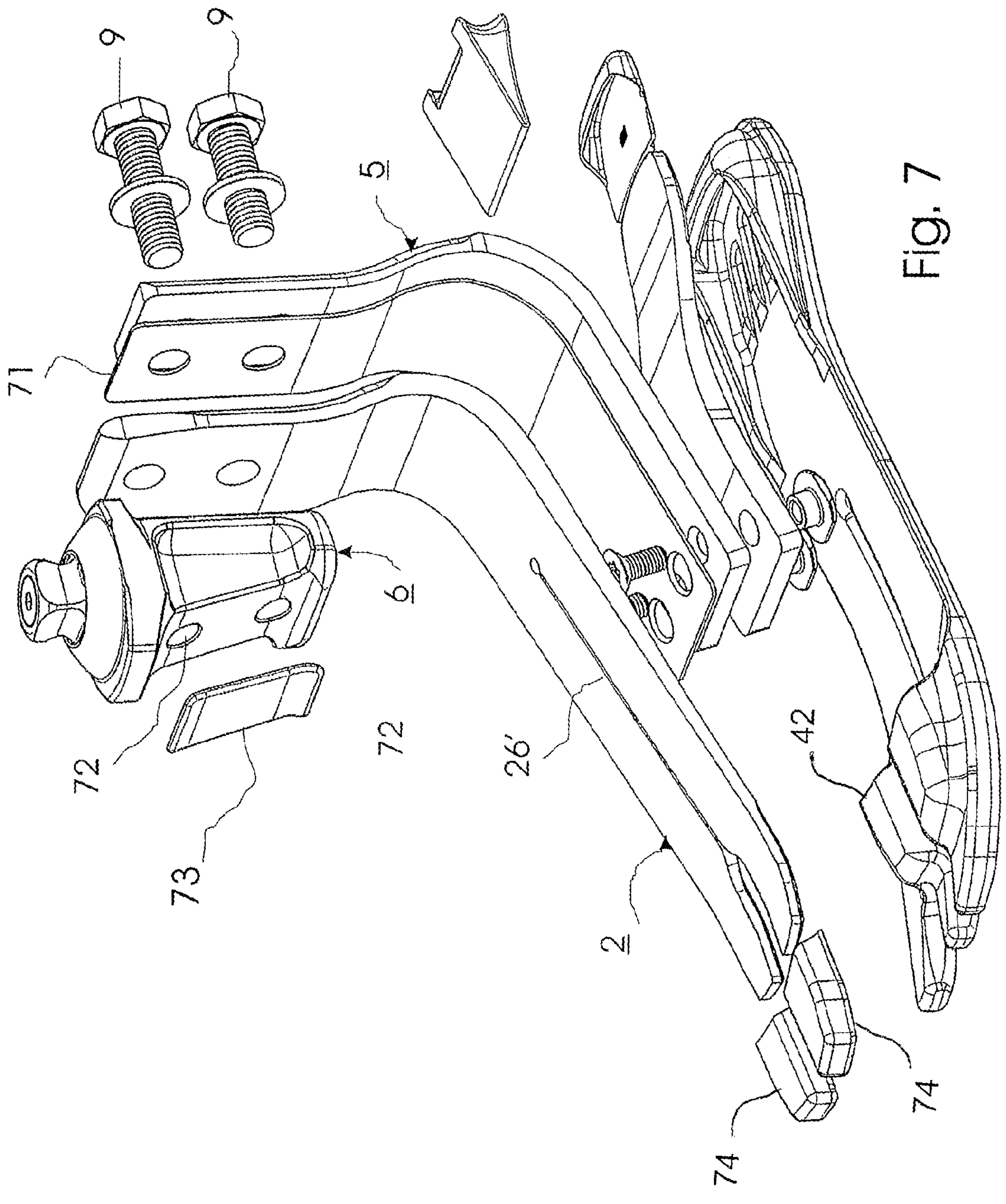
FIG. 7 shows an exploded and perspective view of a further embodiment of the invention.

FIG. 7 illustrates further refinements of the invention. As illustrated in FIG. 7, a friction element 71 is inserted between the forefoot spring 2 and the coupling element 5. The purpose of this friction element 71 is to eliminate or reduce noise. In addition, the forefoot spring has an elongated slit 26' which provides more flexibility in rollover. In the embodiment shown in FIG. 7, the bolts 9 attach to adapter 6 by means of threaded through holes 72. These holes are covered by a cover plate 73, made of any suitable material such as composite or metal. The cover plate 73 may be attached as a friction fit into grooves in the adapter 6 or by adhesive. Caps 74 are shown at the front end of the forefoot spring 2. In the embodiment shown in FIG. 7, the forefoot spring 2 is more or less flat and the caps 74 have corresponding receiving means. Because of the longitudinal slits in the forefoot spring 2 and the base spring 4, it is possible that the springs rotate relative to each other in a way that the inserted forefoot spring 2 is turned inside the receiving pockets 42 of the base spring 4. To minimize the torsional stress along the longitudinal axis of the forefoot spring 2, it is advantageous to allow a relative rotation movement between the caps 74 and the corresponding receiving pockets 42. To achieve this, a conical or cylindrical design is provided, so that the outer surface of the caps can rotate inside the receiving pockets. A stop can be implemented to set a limit for the turning movement.

Figure 7A:
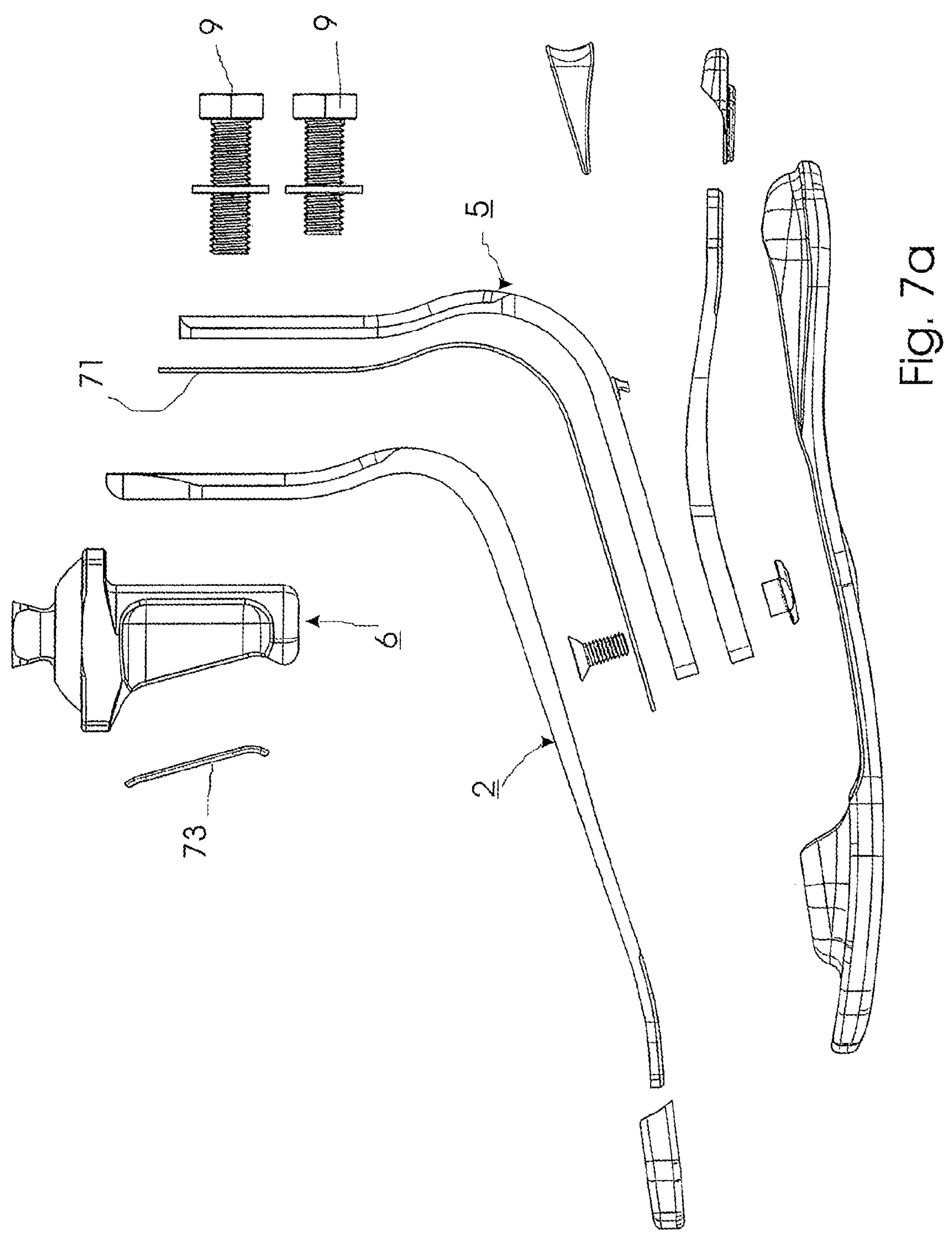
FIG. 7*a* shows an exploded side view of the embodiment of FIG. 7.
Figure 7B:
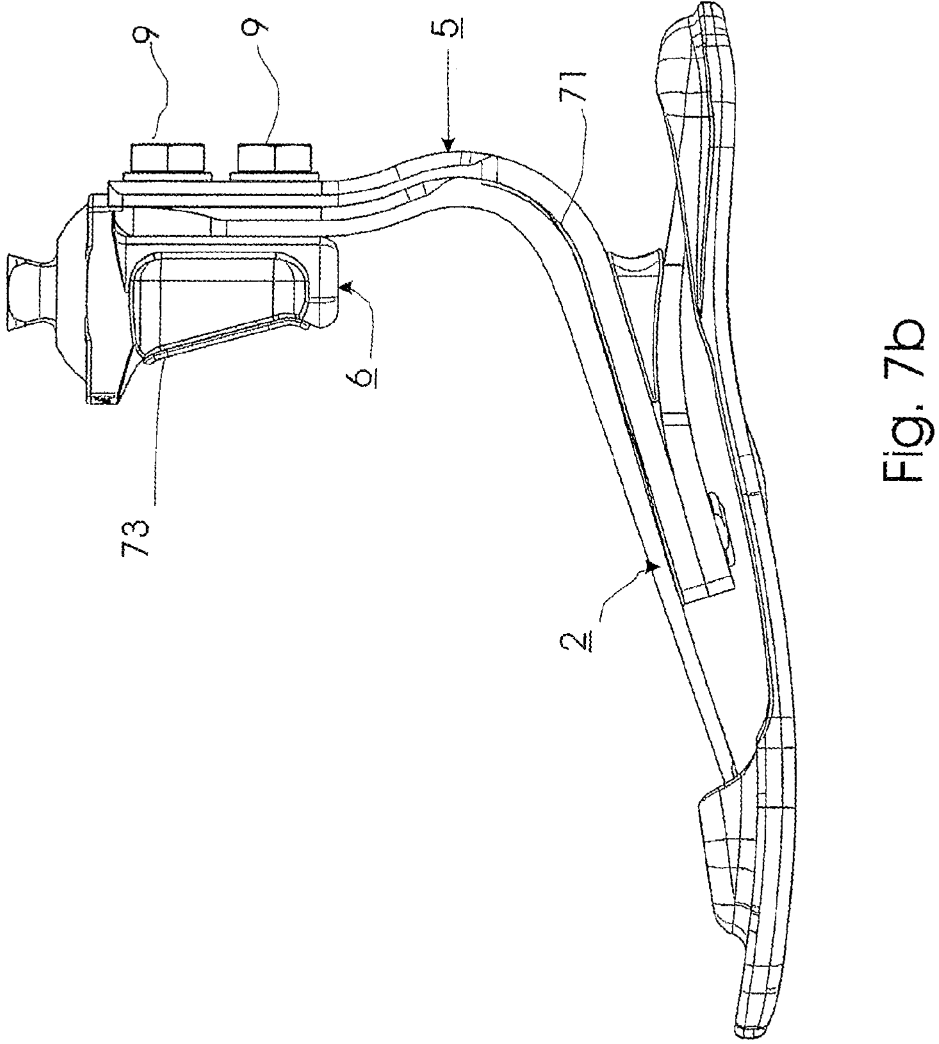
FIG. 7*b* shows a side view of the assembled embodiment of FIG. 7.

FIGS. 7*a* and 7*b* are side views of the embodiment shown in FIG. 7 in an unassembled state and an assembled state, respectively.

Figure 8:
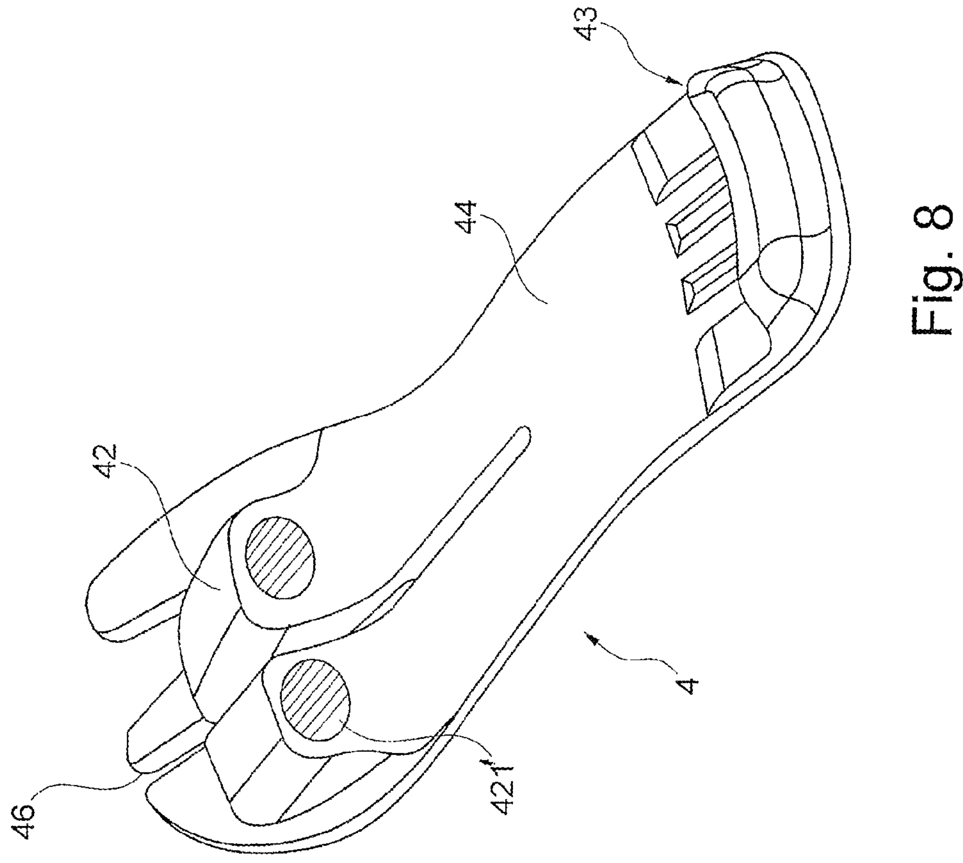
FIG. 8 illustrates a modified base spring having cylindrical or frustro-conical receiving means for receiving ends of the forefoot spring.

FIG. 8 illustrates a modification of the base spring 4, similar to the embodiment in FIG. 4*a* but in which the receiving pockets 42 are provided with cylindrical or frusto-conical insertion openings 421' into which ends of the base spring 4 are inserted.

Figure 9:
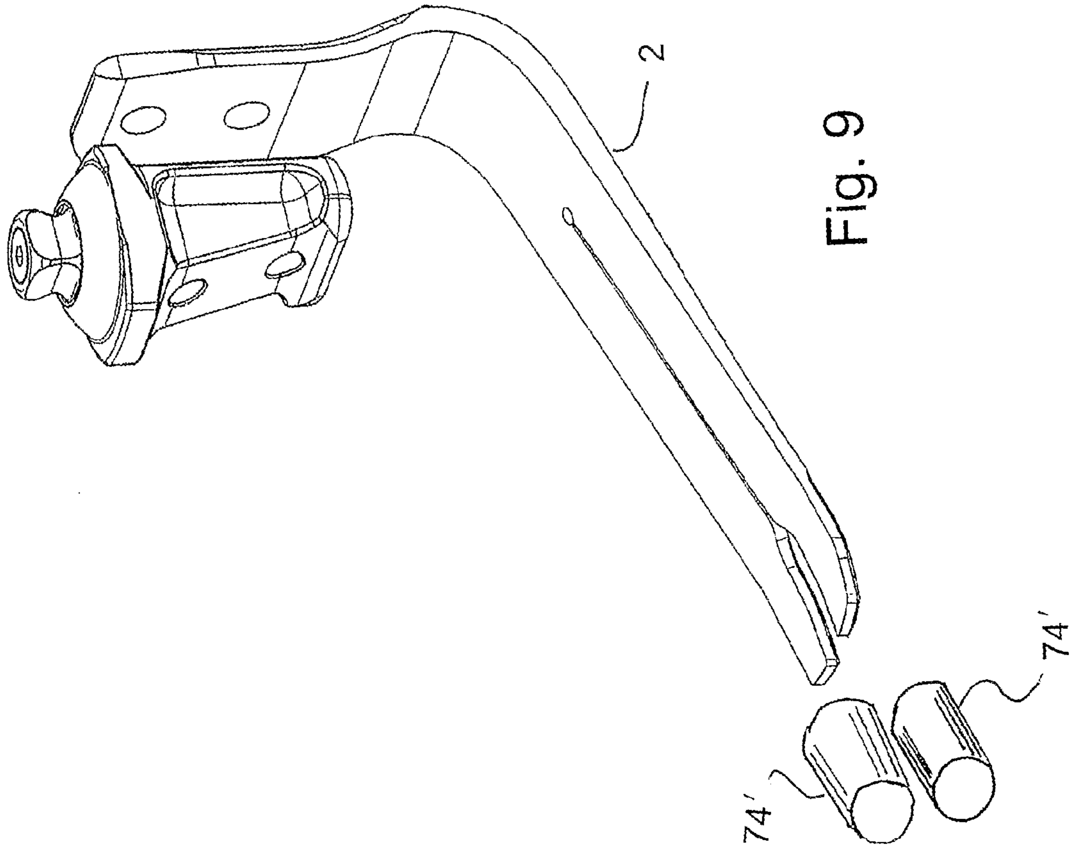
FIG. 9 illustrates a further variation of the caps shown in the FIG. 7 embodiment.

FIG. 9 shows a variation of the embodiment of FIG. 7 in which the caps 74' are cylindrical or frusto-conical.

While the invention has been described in terms of preferred embodiments, those skilled in the art will recognize that the invention can be practiced with modification within the spirit and scope of the appended claims.

The invention claimed is:

1. A prosthetic foot comprising:

a forefoot spring, a heel spring, a base spring having a toe end and a heel end, wherein the base spring is attached to or attachable to the forefoot spring and the heel spring, and at least one pocket formed on or connected to the base spring towards the toe end of the base spring, wherein the at least one pocket is configured as a closed design having a closed rear side, a closed top side, a closed bottom side, a closed left side, a closed right side, and an insertion opening at a front side oriented towards the heel end of the base spring, and wherein the forefoot spring has a toe end which is insertable into the insertion opening of the at least one pocket to attach the forefoot spring to the base spring, and wherein the closed design of the at least one pocket covers the toe end of the forefoot spring when inserted into the insertion opening, and wherein the forefoot spring and the heel spring are tensioned against each other and hold the base spring under tensile stress when the toe end of the forefoot spring is inserted into the insertion opening.

2. The prosthetic foot of claim 1 wherein the at least one pocket is integrally molded with the base spring.

3. The prosthetic foot of claim 1 wherein the base spring comprises a composite midsection and molded ends.

4. The prosthetic foot of claim 1 wherein the base spring comprises recesses.

5. The prosthetic foot of claim 4 wherein the recesses are configured for accommodating screws.

6. The prosthetic foot of claim 1 wherein the base spring, heel spring, and forefoot spring are attachable together without fasteners or glue.

7. The prosthetic foot of claim 1 wherein the base spring, heel spring, and forefoot spring are attachable by plug in connections with each other.

8. The prosthetic foot of claim 7 wherein the base spring has a sandal toe on the toe end which is injection molded.

9. The prosthetic foot of claim 1 wherein the at least one pocket comprises both a first toe pocket on a medial portion of the base spring and a second toe pocket on a lateral portion of the base spring.

10. The prosthetic foot of claim 9 wherein the base spring has a sandal toe on the toe end, and wherein the first toe pocket and the second toe pocket are on opposite sides of the sandal toe.

11. The prosthetic foot according to claim 1, wherein the at least one toe pocket comprises two toe pockets separated by a slit into a medial toe pocket and a lateral toe pocket.

12. The prosthetic foot according to claim 1, wherein the forefoot spring has a substantially straight forefoot portion which, towards a front, is oriented at a downward incline.

13. The prosthetic foot according to claim 1, wherein the at least one pocket holds the toe end of the forefoot spring with a form fit.

14. The prosthetic foot according to claim 1, further comprising at least one heel pocket formed on or connected to the base spring towards the heel end of the base spring, and wherein the heel spring has a heel end which is insertable into an insertion opening of the at least one heel pocket to attach the heel spring to the base spring, and wherein the at least one heel pocket is configured as a closed design having a closed rear side, a closed top side, a closed bottom side, a closed left side, a closed right side, and an insertion opening at a front side oriented towards the toe end of the base spring, and wherein the closed design is configured to cover the toe end of the heel spring when inserted into the insertion opening of the at least one heel pocket.

15. The prosthetic foot according to claim 14 wherein the at least one heel pocket holds the heel spring with a form fit.

16. The prosthetic foot of claim 14 wherein the at least one heel pocket is integrally molded with the base spring.

17. The prosthetic foot according to claim 1, wherein a connecting means, provided for securing the prosthetic foot to a below-knee socket, is arranged on a proximal end of the prosthetic foot.

18. The prosthetic foot according to claim 17, wherein the connecting means has a shock absorber.

19. The prosthetic foot according to claim 17, wherein the forefoot spring is designed as a straight flat spring, and the connecting means is arranged at a rear portion of the forefoot spring.

20. The prosthetic foot according to claim 1, wherein the forefoot spring and the base spring each have a slit.

* * * * *